(12) United States Patent
Gonzalez-Hernandez

(10) Patent No.: US 12,232,970 B2
(45) Date of Patent: Feb. 25, 2025

(54) IMPLANT FACILITATING UPPER HUMERUS RESURFACING AND METHOD FOR USE AND IMPLANTATION THEREOF

(71) Applicant: Eduardo Gonzalez-Hernandez, Miami, FL (US)

(72) Inventor: Eduardo Gonzalez-Hernandez, Miami, FL (US)

(*) Notice: Subject to any disclaimer, the term of this patent is extended or adjusted under 35 U.S.C. 154(b) by 858 days.

(21) Appl. No.: 17/103,146

(22) Filed: Nov. 24, 2020

(65) Prior Publication Data
US 2021/0196466 A1    Jul. 1, 2021

Related U.S. Application Data

(60) Provisional application No. 62/953,679, filed on Dec. 26, 2019.

(51) Int. Cl.
*A61F 2/40*    (2006.01)
*A61F 2/30*    (2006.01)

(52) U.S. Cl.
CPC .......... *A61F 2/4081* (2013.01); *A61F 2/4003* (2013.01); *A61F 2002/30128* (2013.01); *A61F 2002/30242* (2013.01); *A61F 2002/3069* (2013.01); *A61F 2002/4007* (2013.01); *A61F 2002/4085* (2013.01); *A61F 2002/4088* (2013.01)

(58) Field of Classification Search
CPC ................. A61F 2/3603; A61F 2/4003; A61F 2002/4007; A61F 2002/4088
See application file for complete search history.

(56) References Cited

U.S. PATENT DOCUMENTS

| | | |
|---|---|---|
| 4,261,062 A | 4/1981 | Amstutz et al. |
| 4,865,605 A | 9/1989 | Dines et al. |
| 4,919,670 A | 4/1990 | Dale et al. |
| 5,489,309 A | 2/1996 | Lackey et al. |
| 5,944,757 A * | 8/1999 | Grammont ............... A61F 2/40 128/898 |
| 6,187,050 B1 | 2/2001 | Khalili et al. |
| 6,197,062 B1 | 3/2001 | Fenlin |
| 6,508,840 B1 | 1/2003 | Rockwood, Jr. et al. |
| 6,679,916 B1 | 1/2004 | Frankle et al. |
| 6,699,289 B2 | 3/2004 | Iannotti et al. |
| 6,719,799 B1 | 4/2004 | Kropf |
| 6,783,549 B1 | 8/2004 | Stone et al. |

(Continued)

*Primary Examiner* — Megan Y Wolf
(74) *Attorney, Agent, or Firm* — Martin & Ferraro, LLP

(57) ABSTRACT

A surface-reconfiguration implant, a method of using the surface-reconfiguration implant, and a method of implantation of the surface-reconfiguration implant that creates an articular surface between an upper portion of a humeral head and a greater tuberosity, and an undersurface of an acromion in shoulders with massive rotator cuff tears is provided. The surface-reconfiguration implant can include a body portion including at least an undersurface and an articular surface, where the undersurface is configured to interface with portions of a proximal humerus to facilitate attachment of the body portion thereto, and portions of the articular surface extend to and/and preferably beyond a normal anatomical shape of portions a humeral head and a greater tuberosity both superiorly and medially when the body portion is attached to the proximal humerus.

15 Claims, 14 Drawing Sheets

(56) References Cited

U.S. PATENT DOCUMENTS

| | | | |
|---|---|---|---|
| 6,790,234 | B1 | 9/2004 | Frankle |
| 6,942,699 | B2 | 9/2005 | Stone et al. |
| 7,044,973 | B2 | 5/2006 | Rockwood, Jr. et al. |
| 7,175,663 | B1 | 2/2007 | Stone |
| 7,462,197 | B2 | 12/2008 | Tornier et al. |
| 7,621,961 | B2 | 11/2009 | Stone |
| 7,648,530 | B2 | 1/2010 | Habermeyer et al. |
| 7,819,923 | B2 | 10/2010 | Stone et al. |
| 7,854,768 | B2 | 12/2010 | Wiley et al. |
| 8,062,376 | B2 | 11/2011 | Shultz et al. |
| 8,236,059 | B2 | 8/2012 | Stone et al. |
| 8,246,687 | B2 | 8/2012 | Katrana et al. |
| 8,317,871 | B2 | 11/2012 | Stone et al. |
| 8,419,798 | B2 | 4/2013 | Ondrla et al. |
| 8,512,410 | B2 | 8/2013 | Metcalfe et al. |
| 8,845,742 | B2 | 9/2014 | Kusogullari et al. |
| 9,512,445 | B2 | 12/2016 | Iannotti |
| 9,579,106 | B2 | 2/2017 | Lo et al. |
| 10,751,190 | B2 | 8/2020 | Humphrey |
| 10,842,512 | B2 | 11/2020 | Bonin, Jr. et al. |
| 2015/0223940 | A1* | 8/2015 | Papadonikolakis ....... A61F 2/40 623/19.14 |
| 2016/0008137 | A1* | 1/2016 | Long ................. A61B 17/1778 623/19.14 |
| 2018/0256217 | A1* | 9/2018 | Dekel ................. A61F 2/30724 |

\* cited by examiner

IMPLANT FACILITATING UPPER HUMERUS RESURFACING AND METHOD FOR USE AND IMPLANTATION THEREOF

CROSS-REFERENCE TO RELATED APPLICATION

This application claims the benefit U.S. Application Ser. No. 62/953,679, filed Dec. 26, 2019, which is hereby incorporated by reference herein in its entirety.

FIELD

The present disclosure is generally related to a device, a method for use thereof, and a method of implantation for creating an articular surface between an upper portion of a humeral head and a greater tuberosity with an undersurface of an acromion in shoulders with massive rotator cuff tears; a device and method for realigning a superiorly migrated humeral head in a shoulder with a massive rotator cuff tear; a device and method for providing a gliding surface that is prominent and protrudes at least at or above the normal bony outline of a superior portion of a humeral head and a greater tuberosity; a device and method for providing a gliding surface that is prominent and protrudes above the eroded bony outline of a superior portion of a humeral head and a greater tuberosity in the setting of early and moderate cuff tear arthropathy (CTA); and/or a device and method for lowering and inferiorly translating a humeral head to tighten a corresponding deltoid muscle and improve the mechanical lever of the deltoid muscle in a shoulder with a massive rotator cuff tear.

BACKGROUND

In orthopedic surgery, in particular in the field of shoulder reconstruction, a frequent ailment relates to tears of the rotator cuff. Acute tears of the rotator cuff tendons may be repairable by a number of techniques most of which require bone anchors into the intended footprint of the torn tendon and multiple sutures onto the torn tendon. Larger tears resulting in the retraction of the rotator cuff tendons represent a difficult challenge. Frequently the retraction of the rotator cuff tendons is severe, and the corresponding muscles undergo irreversible muscle atrophy and fatty infiltration. Once severe muscle-tendon retraction and muscle atrophy/fatty infiltration has taken place, it is very difficult to repair the rotator cuff tendon.

A shoulder with a massive rotator cuff tear will likely degenerate in a specific pattern different than primary glenohumeral joint osteoarthritis. The end-stage degenerative process that begins with a rotator cuff tear has been named cuff tear arthropathy. The abnormalities identified in a shoulder with end-stage CTA can include: (1) large rotator cuff tears with severe retraction and atrophy/fatty infiltration of surrounding muscle, where such atrophy/fatty infiltration is likely irreversible and the muscle can be left with no useful contractile activity; (2) remodeling of a humeral head in its articulation with a glenoid and an undersurface of acromion, where such remodeling results in a typical pattern of "acetabular" formation between the head, the glenoid, and the undersurface of the acromion; and/or (3) severe cartilage loss and arthrosis. While these three anatomic changes are part of CTA, patients also complain of pain and dysfunction to a varying degree. In many instances, the pain becomes disabling and the loss of function is severe.

CTA does not happen overnight. There is a spectrum of shoulder degeneration from a normal shoulder to a shoulder with end-stage CTA. As discussed below, the progression of degenerational changes in the shoulder undergoing degeneration of CTA is illustrated in a sequence in FIGS. 1-5. FIGS. 6 and 7 illustrate prior art remedies for CTA.

FIG. 6 depicts a prior art partial replacement (or hemiarthroplasty) device 10, where only a humeral head has been replaced with a humeral-head prosthetic 12 made of metallic or other highly-polished materials. As depicted in FIG. 6, the humeral-head prosthetic 12 is assembled to an intramedullary stem 14. And the intramedullary stem 14 can be inserted into a medullary canal of a portion of a proximal humerus, and can be fixed in position with medical grade bone cement and/or by a press fit configuration. FIG. 7. depicts a prior art modified partial replacement device 10' with a modified humeral-head prosthetic 12' that has been configured for use in remedying degeneration of CTA, specifically, moderate to advanced stages of CTA (FIGS. 4 and 5), where there is substantial erosion of the greater tuberosity, superior migration of the proximal humerus, and acetabular formation of the glenohumeral joint. In FIG. 7, the CTA humeral-head prosthetic 12' has an extension 16 or portion that is configured to match and replace the proximal portion of the humerus that has been eroded, namely, the eroded greater tuberosity and articulate with the undersurface of the acromion when the shoulder is elevated. As such, the extension 16 has a shape generally corresponding to the shape of the eroded greater tuberosity. The CTA humeral-head prosthetic 12' has more radians (or fractions of radians) of curvature than the humeral-head prosthetic 12, but can retain the same radius of curvature as the humeral-head prosthetic 12. The prior art embodied in FIGS. 6 and 7, namely, hemiarthroplasty and hemiarthroplasty with a CTA head, have limitations. Hemiarthroplasty replacement has had poor clinical outcomes over the years. One important limitation is the difficulty in restoring the proper joint balance and most patients never recover satisfactory functional elevation.

Total shoulder replacement arthroplasty with reverse configuration total shoulder replacement is an alternative to the above-discussed partial replacement (or hem iarthroplasty) and partial articular replacement for remedying more severe degeneration of CTA. In a reverse-configuration total shoulder replacement, a hem i-circular or hemispheric surface is attached to the glenoid and not to the humerus, and a matching cup is attached to the proximal humerus. The reverse configuration causes the proximal humerus to be lowered or translated distally and laterally, and consequently results in tightening of the deltoid muscle and correspondingly giving the deltoid muscle the mechanical advantage for shoulder elevation without the need of the missing torn rotator cuff muscles. In addition, the reverse-configuration total shoulder replacement is very stable because of the congruity between the components. Reverse-configuration total shoulder replacement can be much more advantageous than the more traditional standard anatomic shoulder replacement. Because of the stability afforded thereby, reverse-configuration total shoulder replacement has made other surgical techniques remedying severe rotator cuff tears somewhat obsolete. The above-discussed partial replacement (or hem iarthroplasty) with a CTA humeral-head prosthetic that extends to the greater tuberosity is one such surgical technique that has been largely obsoleted with the advent of reverse-configuration total shoulder replacement. Furthermore, total articular anatomical replacement is also quickly becoming obsolete.

Reverse-configuration total shoulder replacement is a large surgery. It is a surgery that is best done by surgeons trained not only in orthopedic surgery, but also with additional specialty training in shoulder surgery. A reverse-configuration total shoulder replacement surgery has associated risks including bleeding, nerve, and vascular injury due to the traction necessary to accomplish the exposure and implantation of the components.

Perhaps the more substantial objection to a reverse-configuration total shoulder replacement is the limitations that are placed on the patient after the surgery. A patient on which a reverse-configuration total shoulder replacement has been performed has to restrict his/her activity level and become substantially more sedentary. Riding a bicycle, lifting heavy objects, and medium manual work including repetitive lifting as in carpentry, mechanic work, farming, etc., are out of the question in the short term. In addition, for a patient on which a reverse-configuration total shoulder replacement has been performed, falling down could result in a periprosthetic fracture about the metal components requiring complex revision surgery.

At the present time, there is a substantial need for an alternative to a reverse-configuration total shoulder replacement in younger patients and in elderly patients who want an active lifestyle, who have massive rotator cuff tears that cannot be repaired reliably and have developed degenerative changes of early and moderate rotator cuff arthropathy, i.e., those with massively retracted cuff tears with superior migration of the humeral head and having a salvageable glenohumeral joint with glenohumeral joint cartilage preservation.

There are surgical procedures for early and moderate rotator cuff arthropathy that do not yield consistent reliable results. One such surgical procedure is to grind the greater tuberosity to an even surface to facilitate the sliding of the bone-to-bone surface of the greater tuberosity on the undersurface of the acromion. Such a procedure is called tuberoplasty. Tuberoplasty does not change the joint alignment and in fact may worsen the superior migration of the humeral head. Another such surgical procedure is named superior capsulodesis. In superior capsulodesis, the surgeon uses a thick patch of soft tissue (for instance allograft or xenograft) to create a superior glenohumeral joint fulcrum to limit superior migration of the humeral head. However, the results of superior capsulodesis also are not consistent. In light of the unreliable results of tuberoplasty and superior capsulodesis, many surgeons opt to treat patients with early and moderate rotator cuff arthropathy with reverse-configuration total shoulder replacement. Thus, the need remains for an alternative to a reverse-configuration total shoulder replacement and other procedures to reliably address patients with early and moderate rotator cuff arthropathy, i.e., those with massively retracted cuff tears with superior migration of the humeral head and having a salvageable glenohumeral joint with glenohumeral joint cartilage preservation.

SUMMARY

The subject of the present disclosure generally relates to creating an articular surface in a shoulder subacromial space via use of a proximal-humerus surface-reconfiguration implant with a prominent articular surface. The proximal-humerus surface-reconfiguration implant can be implanted on an upper portion of a humeral head of a proximal humerus to provide a prominent articular surface. The proximal-humerus surface-reconfiguration implant, a method for use thereof, and a method of implantation can provide for realignment via centralization of a superiorly migrated or subluxed humeral head in the setting of an irreparable rotator cuff tear with a salvageable glenohumeral joint.

In one aspect, the present disclosure provides a surface-reconfiguration implant for creating an articular surface facilitating articulation with an acromion and a glenoid during movement of a shoulder joint, the surface-reconfiguration implant including a body portion including at least an undersurface and an articular surface, the undersurface being configured to interface with portions of a proximal humerus to facilitate attachment of the body portion thereto, portions of the articular surface extending to and/or beyond at least a normal anatomical shape of an upper portion of a humeral head and a greater tuberosity both superiorly and medially when the body portion is attached to the proximal humerus, the articular surface being substantially shaped as portions of one of a sphere and an egg, where, when attached to the proximal humerus, the articular surface contacts an undersurface of the acromion, and correspondingly provides inferior translation of the proximal humerus in the shoulder joint.

In another aspect, the present disclosure provides a surface-reconfiguration implant for creating an articular surface facilitating articulation with an acromion and a glenoid during movement of a shoulder joint, the surface-reconfiguration implant including a body portion an articular surface, the body portion being configured for attachment to portions of a proximal humerus to extend to and/or beyond a normal anatomical shape of an upper portion of a humeral head and a greater tuberosity both superiorly and medially when the body portion is attached to the proximal humerus, the articular surface being substantially doom-shaped, where, when attached to the proximal humerus, the articular surface contacts an undersurface of the acromion, and correspondingly provides inferior translation of the proximal humerus in the shoulder joint.

In yet another aspect, the present disclosure provides a method for implantation of a surface-reconfiguration implant and adjustment of a shoulder joint using the surface-reconfiguration implant to restore functional articulation of the shoulder joint, the method including removing a portion of a proximal humerus including portions a humeral head and a greater tuberosity; contacting an undersurface portion of the surface-reconfiguration implant to a surface of the removed portion of the proximal humerus; attaching the surface-reconfiguration implant to the proximal humerus to cover and extend above a normal anatomical shape of the removed portion of the proximal humerus; and contacting an articular surface of the surface-reconfiguration implant to an undersurface of an acromion of the shoulder joint and a coracoacromial ligament to translate the proximal humerus inferiorly.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
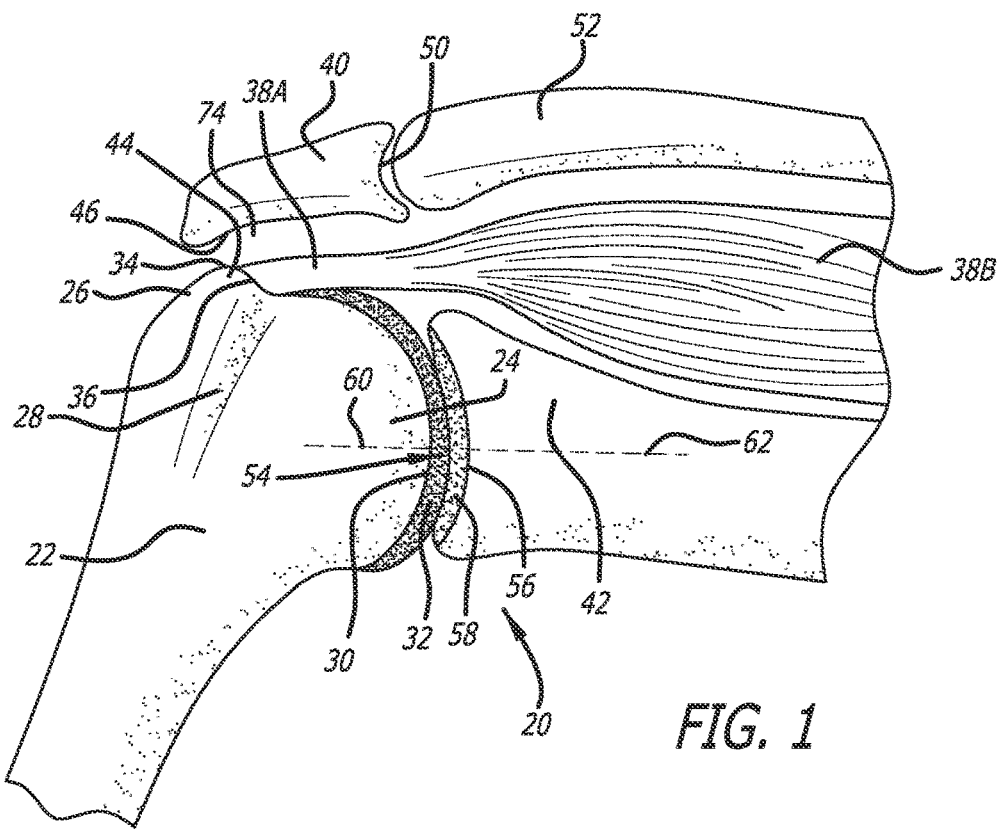
FIG. 1 is a front illustrative view of an ideal human shoulder joint.

The present disclosure contemplates creating an articular surface between an upper portion of a humeral head and a greater tuberosity of a proximal humerus and an undersurface of an acromion. A device according to the present disclosure can take the form of a proximal-humerus surface-reconfiguration implant that can be attached to the upper portion of the humeral head and the greater tuberosity, a method for use thereof, and a method of implantation. The device of the present disclosure can require less surgery than a reverse-configuration total shoulder replacement, and could be done as an outpatient procedure. Unlike the much larger reverse-configuration total shoulder replacement, the device of the present disclosure can potentially require minimal bone excision, minimal bone resection, minimal dissection, minimal traction maneuvers on the shoulder, minimal risk to neurovascular structures, and lesser infection risk, and allow the patient to return relatively quickly to physical activity.

Embodiments of the proximal-humerus surface-reconfiguration implant are generally indicated by the numerals 100, 120, 120', and 130 in FIGS. 10-17. The device according to embodiments of the present disclosure is not a "resurfacing" arthroplasty using devices like the above-discussed devices 10 and 10', but rather a redesign of the upper portion of the humeral head and the greater tuberosity into a prominent gliding surface to centralize the humeral head in the shoulder joint via use of the proximal-humerus surface-reconfiguration implant. As discussed below, the proximal-humerus surface-reconfiguration implants 100, 120, 120', and 130 each create a raised articular surface over the proximal humerus (including upper portions of the humeral head and the greater tuberosity) and at least at or preferably above the normal bony outline of a superior portion of the humeral and the greater tuberosity, and serves to at least translate the humeral head inferiorly. Contact of the raised articular surfaces of the proximal-humerus surface-reconfiguration implants 100, 120, 120', and 130 with the undersurface of the acromion serves to translate the humeral head inferiorly, which serves to reposition the humerus relative to the remainder of the shoulder joint to improve anatomical congruity.

Unlike use of the CTA humeral-head prosthetics 12 and 12', or even a tuberoplasty, all of which pretend to match the eroded surface of the greater tuberosity and that of the humeral head in shoulders with degeneration of CTA, and where the proximal humerus has been remodeled substantially to basically a "single" round surface after substantial erosion of the greater tuberosity, the proximal-humerus surface-reconfiguration implant of the present disclosure is a prominent surface extending superiorly at and/or preferably beyond the normal contours of an upper portion of a humeral head and a greater tuberosity before severe erosion of the greater tuberosity occurs.

Via interaction of the raised articular surface thereof with the undersurface of the acromion, the proximal-humerus surface-reconfiguration implant serves in translating the humeral head inferiorly. And by translating the humeral head inferiorly, the imbalance of the superiorly migrated humeral head is corrected.

After translation of the humeral head inferiorly using the proximal-humerus surface-reconfiguration implant, the humeral head can be made congruous with the glenoid through the arc of motion. Congruity of the glenohumeral joint is a necessary condition to minimize joint wear and degeneration that otherwise leads to cartilage damage, wear, and end stage arthrosis. In addition, by translating the humeral head inferiorly, the fibers of the deltoid muscle tighten up in a similar fashion as in a reverse-configuration total shoulder replacement.

As depicted in FIG. 1, a shoulder joint 20 of a human shoulder includes a proximal humerus 22, and the proximal humerus 22 includes a humeral head 24, a greater tuberosity 26, and a bicipital groove 28. The shoulder joint 20 depicted in FIG. 1 is ideal. The humeral head 24 includes cortical bone 30, and articular cartilage 32 is provided adjacent the cortical bone 30. The greater tuberosity 26 includes a topmost (or prominent) portion 34 and an insertion site 36. In the ideal shoulder joint 20, a tendinous portion 38A (for instance, the supraspinatus tendon) attached to a muscular portion 38B (for instance, the supraspinatus muscle) of a rotator cuff is attached to the proximal humerus 22 at the insertion site 36.

The shoulder joint 20 also includes portions of a scapula including an acromion 40 and a glenoid 42. As depicted in FIG. 1, portions of the proximal humerus 22 are positioned under the acromion 40, and, while a portion 44 of the greater tuberosity 26 is brought under the acromion 40 with elevation of the shoulder, the portion 44 of the greater tuberosity 26 does not physically articulate with an undersurface 46 of the acromion 40 under normal circumstances.

The acromion 40 forms an acromioclavicular joint 50 with a clavicle 52, and the glenoid 42 forms a glenohumeral joint 54 that is formed by portions of the humeral head 24 and the glenoid 42. The glenoid 42 includes cortical bone 56, and articular cartilage 58 is provided adjacent the cortical bone 56. The glenohumeral joint 54 between the humeral head 24 and the glenoid 42 is formed at the contact of the articular cartilage 32 and 58.

FIG. 1 includes an imaginary line 60 through a mid-portion of the proximal humerus 22, and an imaginary line 62 through the mid-portion of the glenoid 42 to denote an ideal relative alignment of the proximal humerus 22 and the glenoid 42 in the shoulder joint 20. As depicted in FIGS. 2-5, the imaginary lines 60 and 62 become more and more misaligned during the degeneration of CTA.

Figure 2:
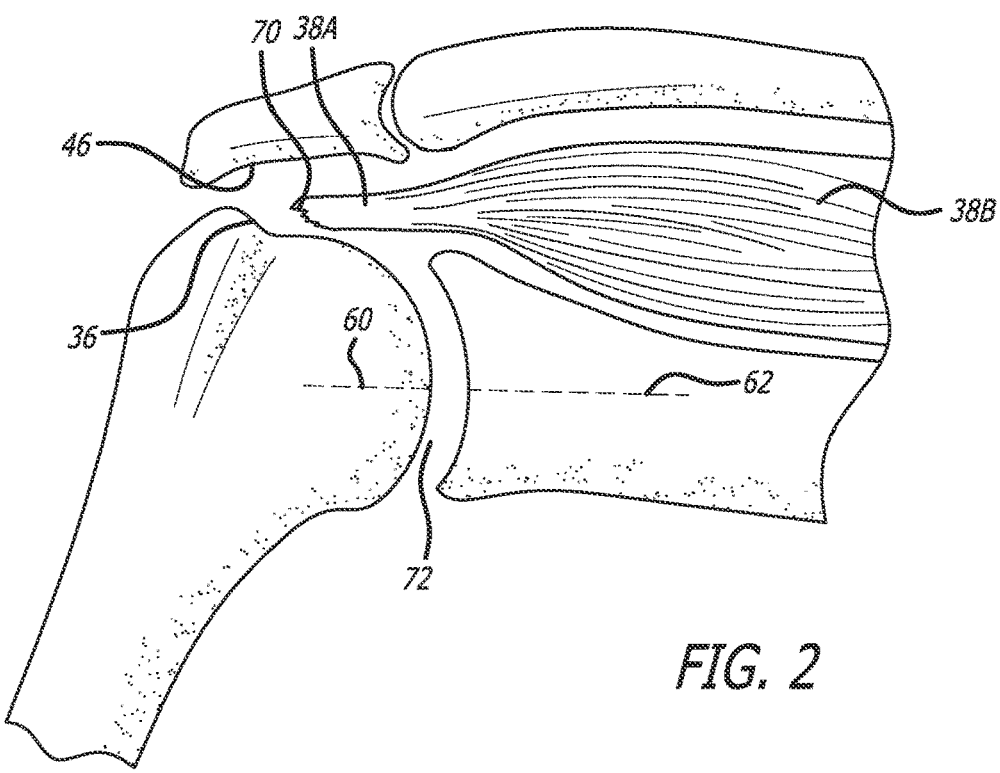
FIG. 2 is a front illustrative view depicting a shoulder joint undergoing degeneration of CTA.

As depicted in FIG. 2, a first stage of the shoulder joint 20 undergoing degeneration of CTA is shown. FIG. 2 depicts a tear of the rotator cuff tendon 38A at a torn edge 70 from the insertion site 36 that initiates the degeneration of CTA. Although the articular cartilage 32 and 58 is not shown, an articular space 72 denotes where the articular cartilage 32 and 58 are present. After such a tear of the rotator cuff tendon 38A, the rotator cuff muscle 38B begins to retract, and such retraction causes muscle atrophy of and fatty infiltration into the rotator cuff muscle 38B. Because the degeneration of CTA has just begun, the retraction of the rotator cuff tendon 38A is not substantial, and the muscle atrophy/fatty infiltration is also not substantial. As such, the proximal humerus 22 and the glenoid 42 remain well aligned as denoted by the alignment of the imaginary lines 60 and 62, and the portions of the humeral head 24 and the glenoid 42 adjacent the articular space 72 remain substantially parallel.

Figure 3:
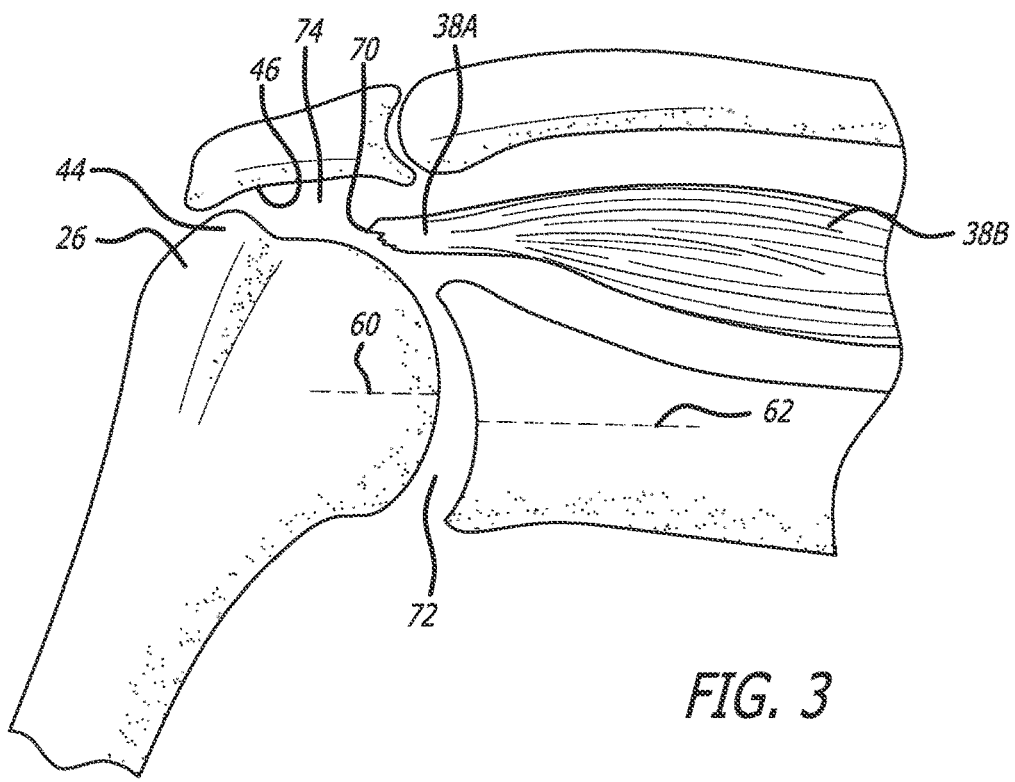
FIG. 3 is a front illustrative view depicting the shoulder joint of FIG. 2 undergoing further degeneration of CTA.

As depicted in FIG. 3, a second stage of the shoulder joint 20 undergoing degeneration of CTA is shown. The degeneration of CTA in FIG. 3 is chronic. FIG. 3 depicts the rotator cuff muscle 38B having undergone substantial muscle atrophy/fatty infiltration. Furthermore, FIG. 3 depicts the humeral head 24 having migrated superiorly with respect to the glenoid 42, and as a result, the imaginary lines 60 and 62 are no longer aligned, and the portions of the humeral head 24 and the glenoid 42 adjacent the articular space 72 are no longer parallel. Given the superior migration of the humeral head 24, the greater tuberosity 26 and the undersurface 46 of the acromion 40 now articulate with respect to one another.

Figure 4:
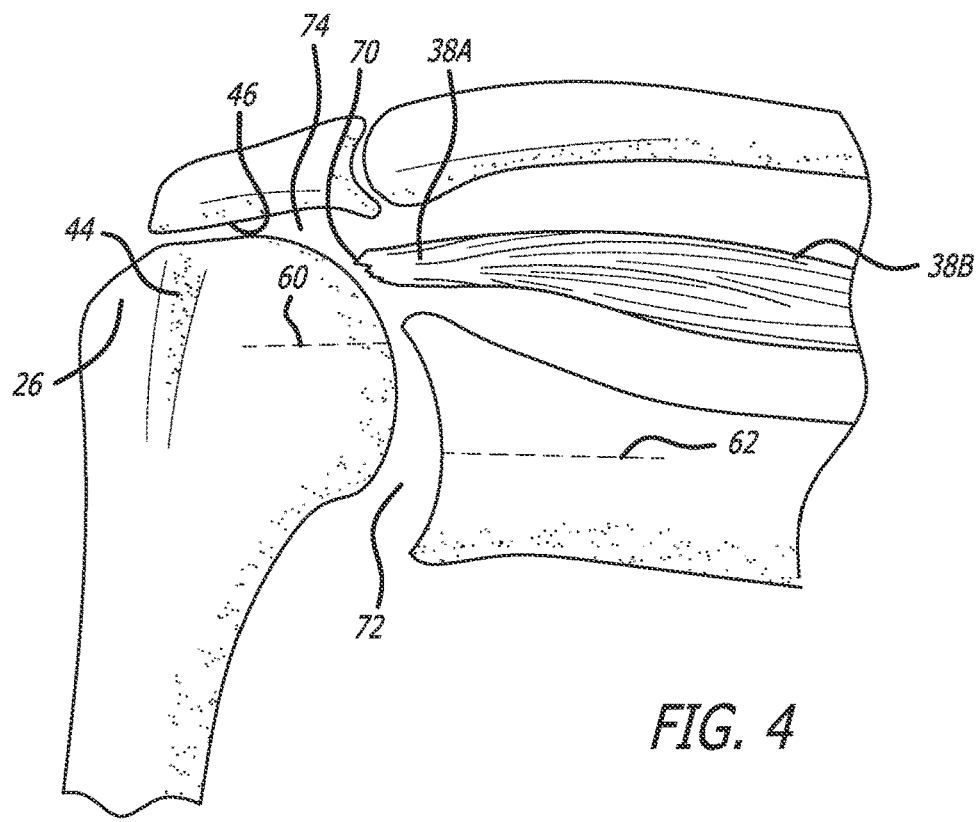
FIG. 4 is a front illustrative view depicting the shoulder joint of FIGS. 2 and 3 undergoing still further degeneration of CTA.

As depicted in FIG. 4, a third stage of the shoulder joint 20 undergoing degeneration of CTA is shown. FIG. 4 depicts substantial blunting of the greater tuberosity 26 due to articulation of the greater tuberosity 26 and the undersurface 46 of the acromion 40 with respect to one another. Such articulation serves in obliterating a subacromial space 74, and, due to the blunting of the greater tuberosity 26, affords further superior migration of the humeral head 24. FIG. 4 depicts the humeral head 24 having further migrated superiorly with respect to the glenoid 42, and as a result, the imaginary lines 60 and 62 are severely misaligned, and portions of the articular space 72 between the portions of the humeral head 24 and the glenoid 42 continue to narrow.

Figure 5:
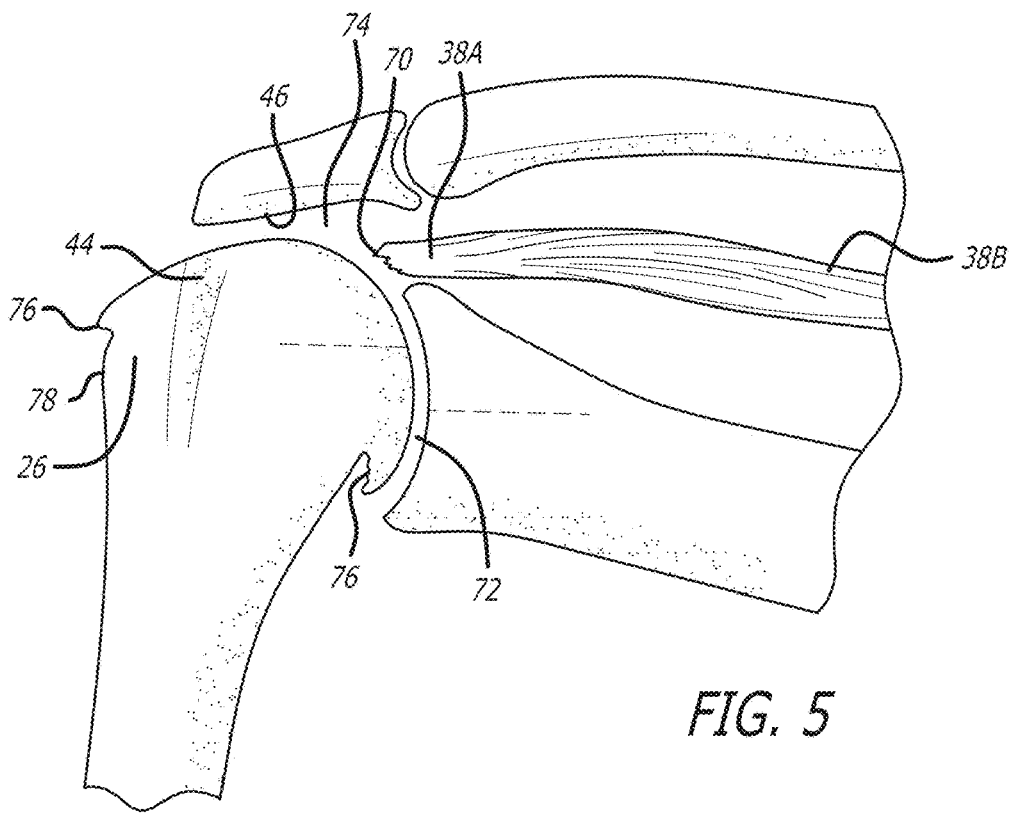
FIG. 5 is a front illustrative view depicting the shoulder joint of FIGS. 2-4 subject to end-stage degeneration of CTA with superior migration and subluxation of a humeral head of a proximal humerus.

As depicted in FIG. 5, a fourth stage of the shoulder joint 20 undergoing degeneration of CTA is shown. The degeneration of CTA in FIG. 5 is end-stage degeneration. FIG. 5 depicts the humeral head 24, the greater tuberosity 26, and the undersurface 46 of the acromion 40 having been remodeled, where the greater tuberosity 26 has been flattened and is basically continuous with the humeral head 24, and the subacromial space 74 has been completely obliterated into an articular space between the humeral head 24, the greater tuberosity 26, and the acromion 40. The glenoid 42 has also been remodeled in addition to the humeral head 24, the greater tuberosity 26, and the acromion 40. The remodeling of the humeral head 24, the greater tuberosity 26, the acromion 40, and the glenoid 42 give rise to a sort of acetabular joint, where bone to bone contact remains. The degeneration of CTA also causes osteophytes 76 and 78 to develop on the proximal humerus.

Figure 6:
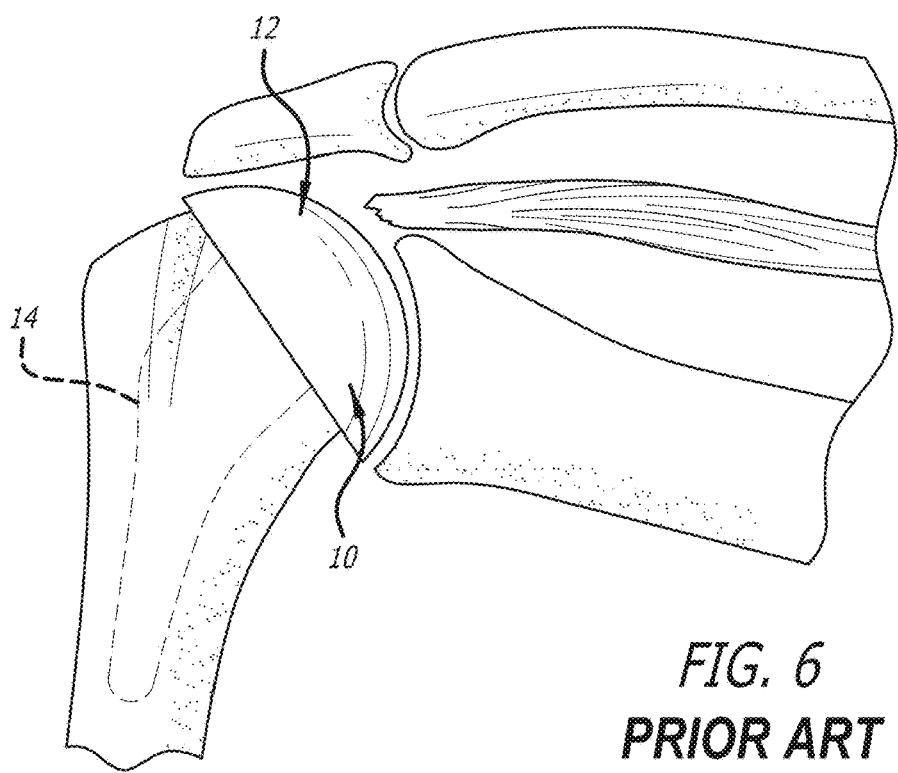
FIG. 6 is a front illustrative view depicting a shoulder joint with a prior art partial replacement (or hem iarthroplasty) device.
Figure 7:
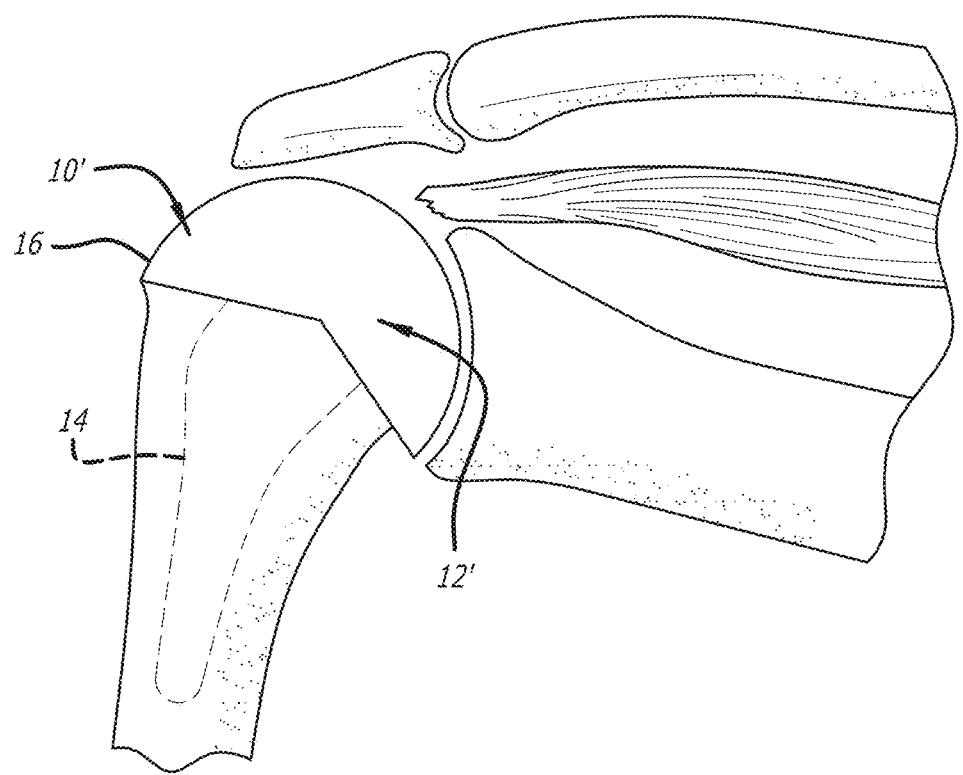
FIG. 7 is a front illustrative view depicting a shoulder joint with a prior art modified partial replacement (or hemiarthroplasty) device with a CTA head.

As discussed above, FIGS. 6 and 7 illustrate prior art remedies for CTA that have proved to be inadequate. As depicted in FIGS. 10-14, the proximal-humerus surface-reconfiguration implants 100, 120, 120', and 130 are provided to address these inadequacies.

Figure 8:
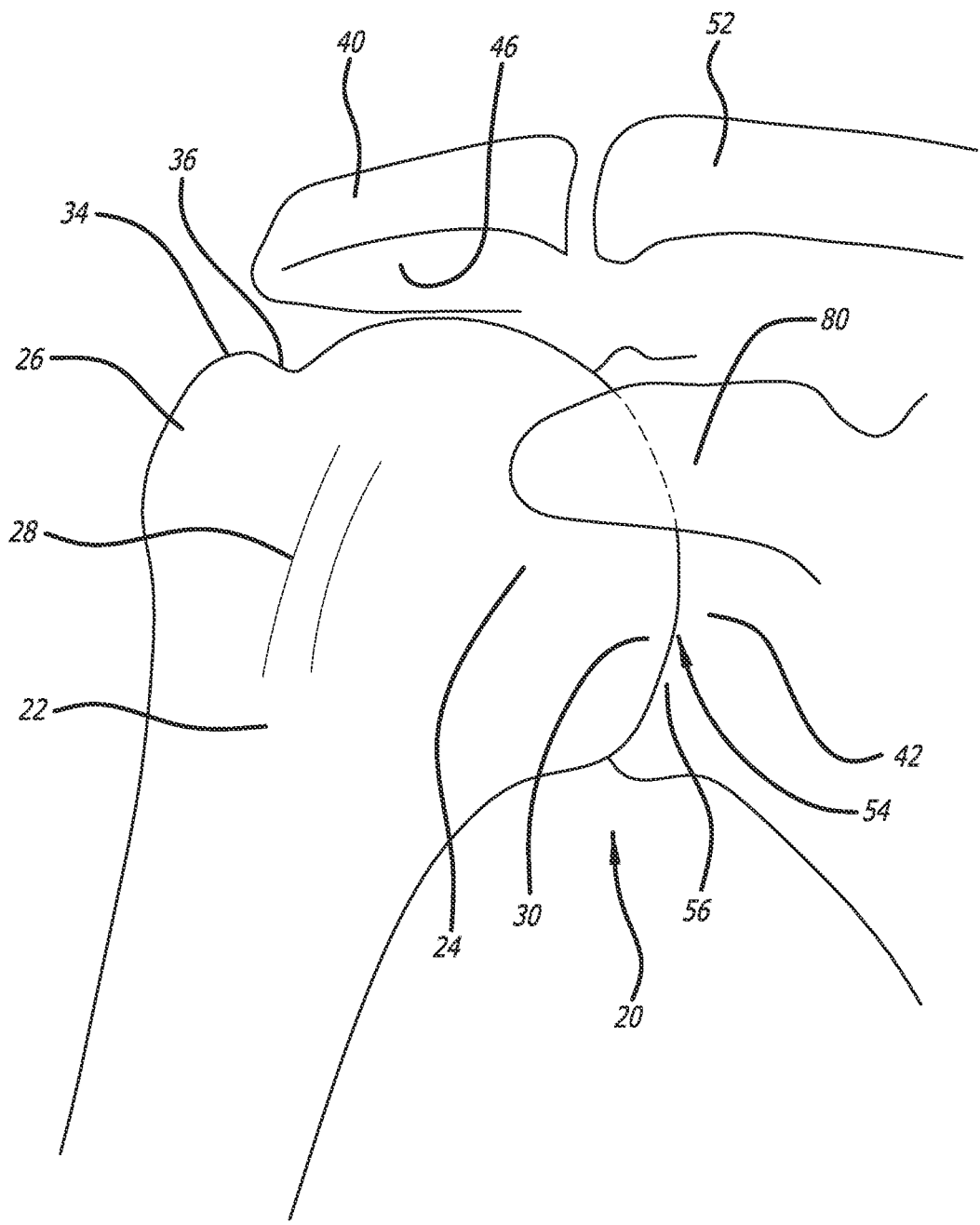
FIG. 8 is a front illustrative view depicting a normal shoulder joint.

FIG. 8 depicts a normal shoulder joint 20. In FIG. 8, the solid outline solid outline describing the proximal humerus 22 and the glenoid 42 include the articular cartilaginous surface. A coracoid process 80 is depicted in FIG. 8 in position relative to the humeral head 24, the acromion 40, the glenoid 42, and the clavicle 52. The center of the humeral head 24 is coincident with the center of rotation of the shoulder joint 20. When the cartilage of the glenohumeral joint 54 has been at least partially preserved, as in early and mid-stage CTA, the surface reconfiguration implants 100, 120, 120', and 130 can be used to address the patient's symptoms of pain and improve shoulder function when the rotator cuff cannot be repaired and in the setting of early to moderate CTA. Unattended, the shoulder joint 20 will follow the sequence of degeneration of CTA.

Figure 9:
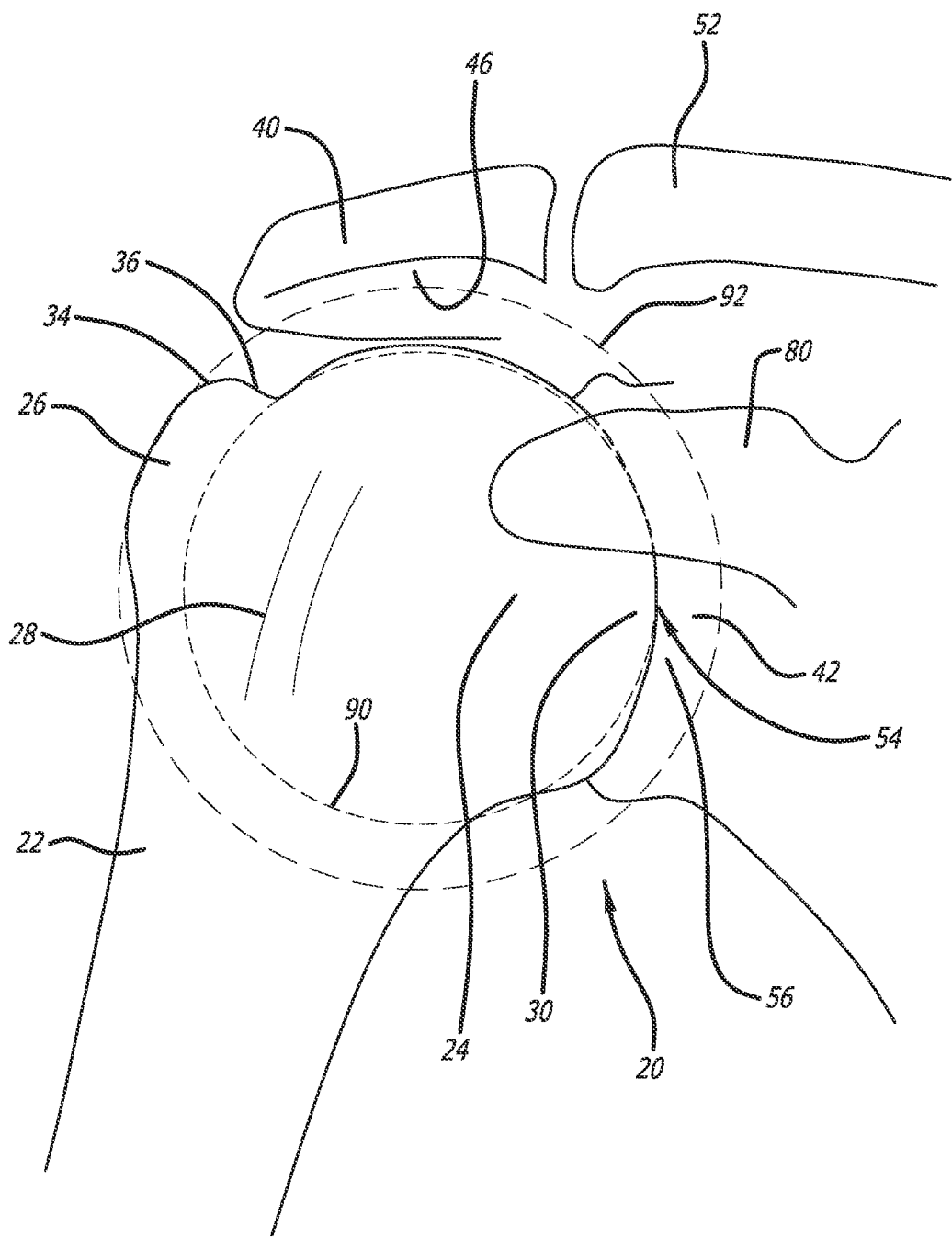
FIG. 9 is a front illustrative view depicting a shoulder joint including concentric circles illustrating relationships between a humeral head, a greater tuberosity, and an undersurface of an acromion using these concentric circles.

FIG. 9 depicts the shoulder joint 20 with the humeral head 24 positioned as in FIG. 8, and showing the relationship between circles 90 and 92. The exterior surface of the humeral head 24 approximates a sphere, and the circle 90 follows the outline of the humeral head 24. As illustrated by the circle 90, the center of rotation of the humeral head 24 is coincident with the center the humeral head 24 under normal circumstances without imbalance or subluxation thereof. The circle 92 has a radius extending (from the center of the humeral head 24) to the greater tuberosity 26. The circle 92 illustrates a potential path of the greater tuberosity 26 under the acromion 40 during articulation of the shoulder 20 with imbalance or subluxation thereof. Under normal circumstances, the circle 92 (corresponding to the greater tuberosity) does not reach the undersurface 46 of the acromion 40 during articulation of the shoulder joint 20. However, when the humeral head 24 is superiorly migrated or subluxed, the circle 92 can potentially intersect with the acromion 40, which can result in the above-discussed degeneration of CTA, thereby causing interaction of the greater tuberosity 26 with the undersurface 46 of the acromion 40.

The surface-reconfiguration implants 100, 120, 120', and 130, as depicted in FIGS. 10-14, provide articulation via smooth gliding contact between the articular surfaces thereof and the undersurface 46 of the acromion 40. Furthermore, the implants 100, 120, 120', and 130 facilitate remediation of the degeneration of CTA by facilitating inferior repositioning of the humeral head 24 relative to the acromion 40 and the glenoid 42 to concentrically reduce the glenohumeral joint.

The surface-reconfiguration implants 100, 120, and 130, as discussed below, can be attached relative to the proximal humerus 22 using mechanical fasteners, adhesives, and/or using an interference fit via insertion into a portion of the proximal humerus. Mechanical fasteners in the form one or more screws can, for example, be inserted into apertures provided in the surface-reconfiguration implants and into the proximal humerus to facilitate attachment between the surface-reconfiguration implants and the proximal humerus. Furthermore, adhesives can, for example, be provided between undersurfaces of the surface-reconfiguration implants and a portion of the proximal humerus to facilitate attachment between the surface-reconfiguration implants and the proximal humerus. And interference fits can, for example, be provided between posts or spikes extending outwardly from undersurfaces of the surface-reconfiguration implants and channels or apertures formed in the proximal humerus to facilitate attachment between the surface-reconfiguration implants and the proximal humerus. While the fasteners and the posts/spikes are further discussed below, these types of attachment can be combined with one another to secure attachment of the surface-reconfiguration implants to the proximal humerus.

After implantation, the surface-reconfiguration implants 100, 120, 120', and 130 provide prominent mounds or bumps with raised articular surfaces that are at least in part domed and that serve in realigning the glenohumeral joint and providing articulation via smooth gliding contact between the articular surfaces thereof and the undersurface 46 of the acromion 40. Furthermore, the surface-reconfiguration implants 100, 120, 120', and 130 narrowly "overstuffs" what once was the subacromial space 74, which serves in translating the center of the humeral head 24 distally. The fibers of the deltoid muscle (not shown) are tensioned by translating the center of the humeral head 24 distally. Putting the deltoid fibers in tension provides for improved mechanics for articulation of the shoulder joint 20 in similar fashion to that of a reverse-configuration total shoulder replacement. Under tension, the deltoid muscle is a capable elevator of the shoulder joint. As such, the surface-reconfiguration serves to reposition the humerus relative to the remainder of the shoulder joint 20 to improve anatomical congruity.

Figure 10:
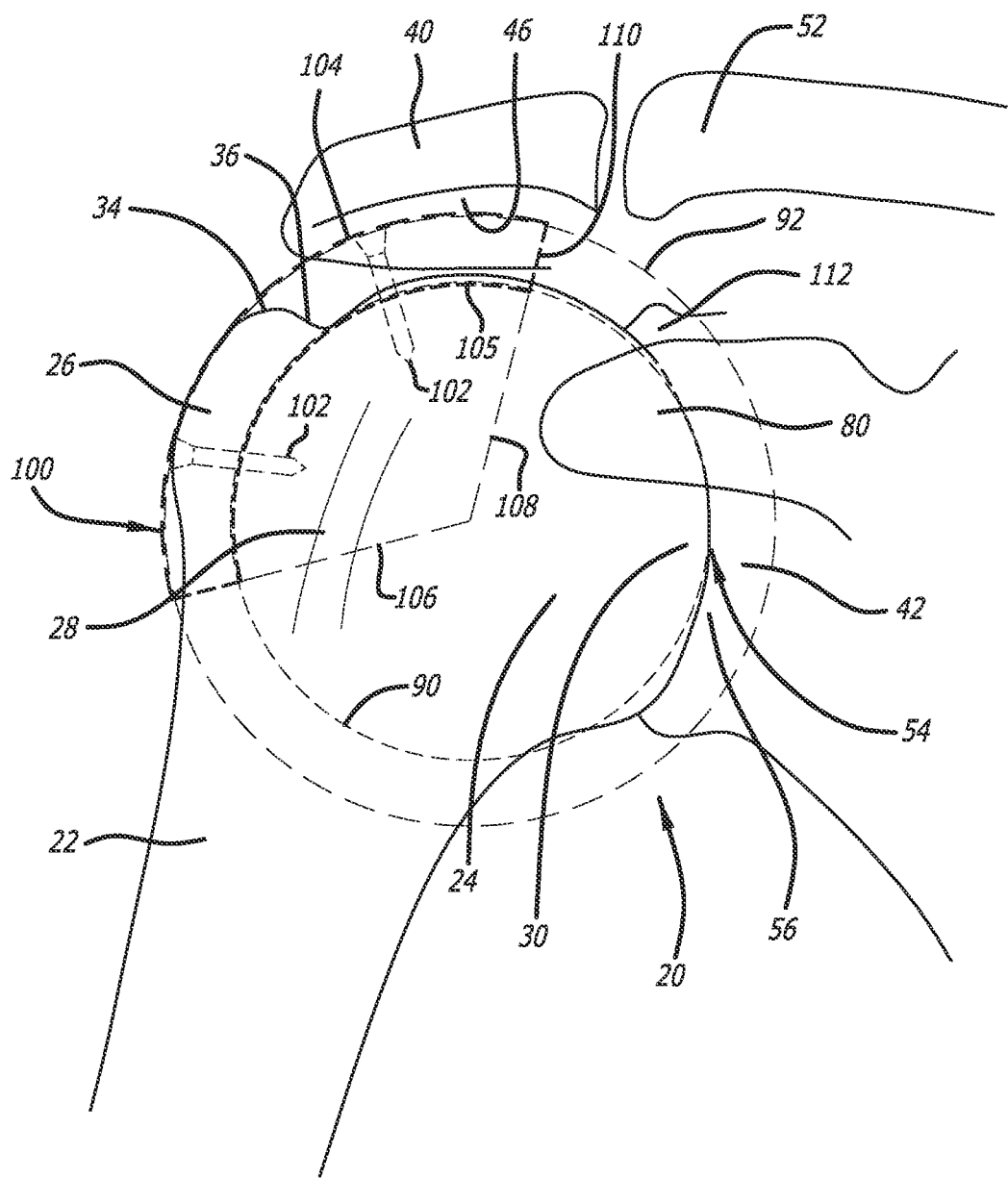
FIG. 10 is a front illustrative view depicting a first embodiment of a proximal-humerus surface-reconfiguration device according to the present disclosure in position relative to a shoulder joint.

FIG. 10 depicts the first embodiment 100 of the surface-reconfiguration implant. The implant 100 is shown in cross-section, and, as depicted in FIG. 10, the implant 100 extends within or just slightly out of the space between the circles 90 and 92. The implant 100 is positioned superiorly into the proximal humerus 22. The implant 100 can be implanted within the proximal humerus 22, and attachment of the implant 100 to the proximal humerus 22 can be effectuated using fasteners 102. To effectuate such attachment, portions of the proximal humerus 22 including the humeral head 24 and the greater tuberosity 26 may require removal. As depicted in FIG. 10, the implant 100 can be formed from a metallic plate that can be shaped as a substantially spherical cap, and that can be sized to overlap the greater tuberosity 26 (or at least portions of the remnants of the greater tuberosity 26) and overlap portions of the humeral head 24 (or at least portions of the remnants of the humeral head 24). In doing so, the implant 100 effectively covers and extends above areas where the portions of the humeral head 24 and the greater tuberosity 26 were or are located.

The implant 100 includes a raised articular surface 104 and an undersurface 105. Although shown in cross-section in FIG. 10, the articular surface 104 can be biconcave and be substantially dome-shaped as portions of a sphere or an egg, and portions thereof can be configured to at least extend to and/or beyond the normal (undamaged) anatomical shape of the greater tuberosity 26 both superiorly and medially. For example, with the implant 100 positioned relative to the proximal humerus 22, portions of the articular surface 104 preferably can be between approximately 0-5 mm up to 6 mm and even 7 mm higher in a superior direction than the maximum normal (undamaged) anatomical height and bony outline of the greater tuberosity 26, and approximately 2-5 mm up to 6 mm and even 7 mm higher in a superior direction than the maximum normal (undamaged) anatomical height and bony outline of the humeral head 24. Furthermore, the undersurface 105 is configured to contact portions of the proximal humerus 22.

As depicted in FIG. 10, the articular surface 104 corresponds to the outermost circle of the circle 92, and extends in an arc between dashed lines 106 and 108. The articular surface 104 articulates by sliding with respect to the undersurface 46 of the acromion 40. In doing so, the protrusion formed by the articular surface 104 serves in moving the proximal humerus 22 inferiorly to facilitate centralization of the humeral head 24 in the shoulder joint 20 through a useful range/arc of shoulder elevation. A medial leading edge portion 110 may run into and erode an upper edge 112 of the glenoid 42 if the humerus elevated too high during articulation of the shoulder joint 20. As such, the plate forming the implant 100 can be thinned at and adjacent the medial leading edge portion 110, and can also be configured to smoothly blend into the remaining portions of the proximal humerus 22 and/or cartilage of the glenohumeral joint 54 adjacent the medial leading edge portion 110 to prevent such erosion if contacted to the upper edge 112.

FIGS. 11-14 depict the second embodiment 120 of the surface-reconfiguration implant. Like the implant 100, the implant 120 is attached to the proximal humerus 22, overlaps portions of the humeral head 24 and overlaps the greater tuberosity 26, and effectively covers and extends above areas where the portions of the humeral head 24 and the greater tuberosity 26 were or are located. The implant 120 can be partially shaped as a substantially spherical cap. The attachment of the implant 120 to the proximal humerus 22 can be effectuated with fasteners 122 (FIG. 12) such as bone screws.

Figure 11:
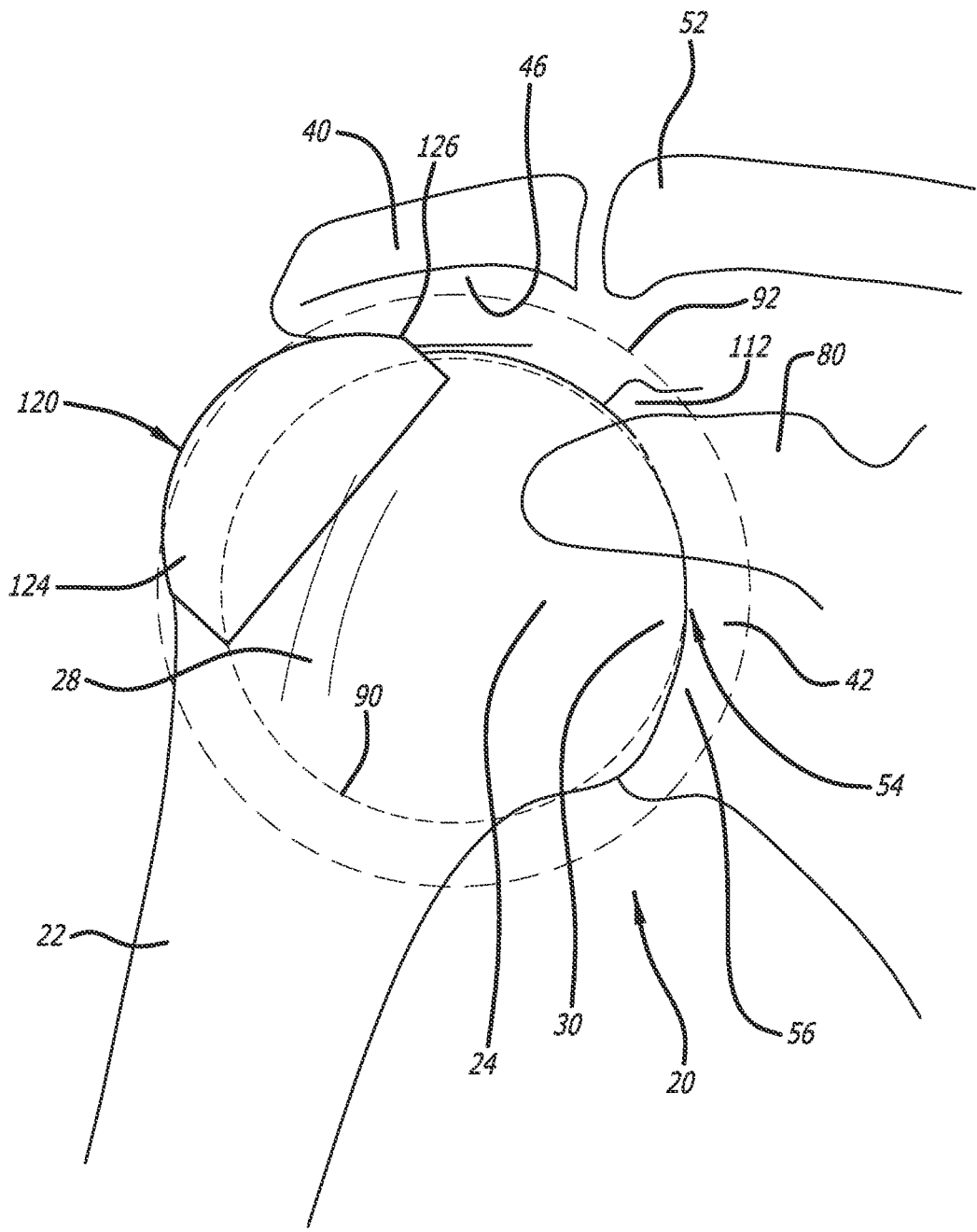
FIG. 11 is a front illustrative view depicting a second embodiment of a proximal-humerus surface-reconfiguration device according to the present disclosure in position relative to a shoulder joint.
Figure 12:
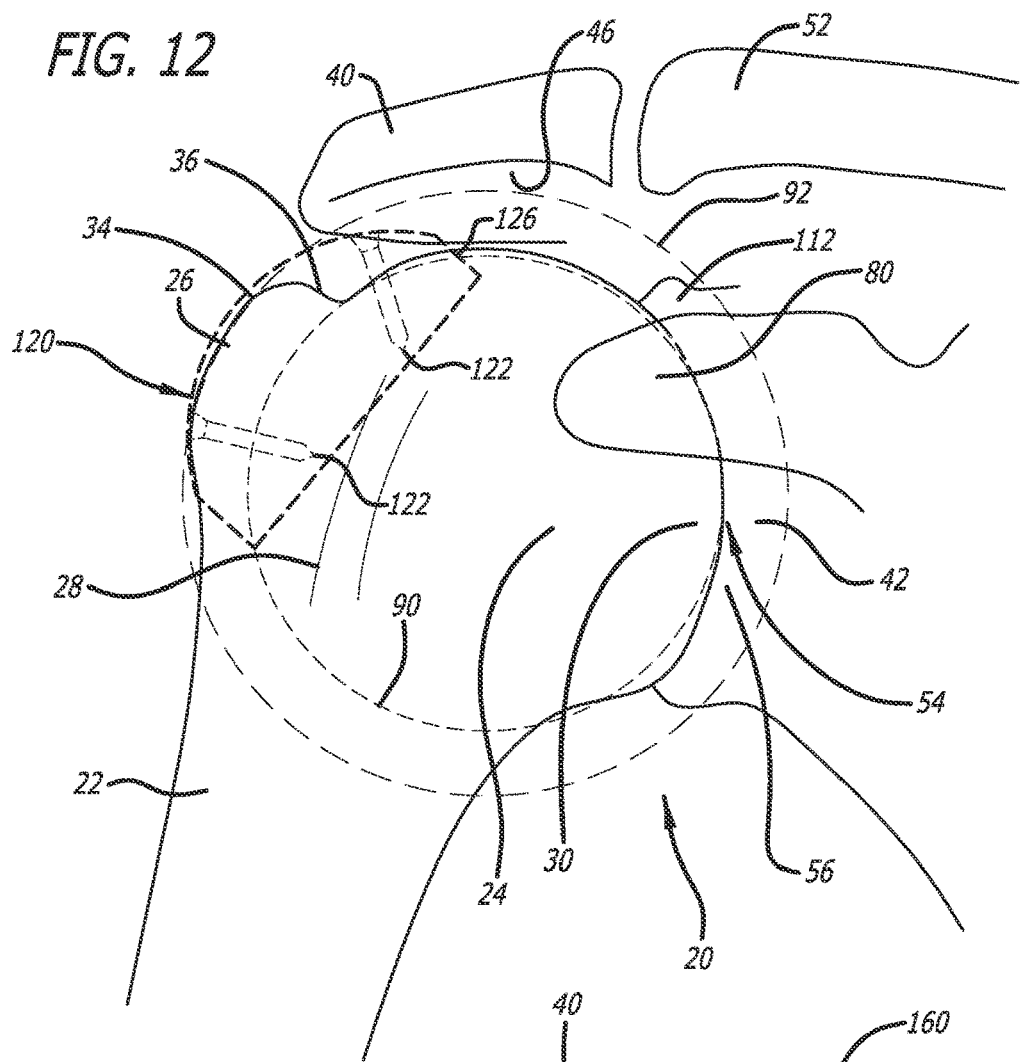
FIG. 12 is a front illustrative view similar to FIG. 11 depicting the second embodiment of the proximal-humerus surface-reconfiguration device in phantom.

As depicted in FIGS. 11 and 12, the implant 120 includes a raised articular surface 124, and the articular surface 124 extends along portions of and within or just slightly out the outermost circle of the circle 92. The articular surface 124 can be biconvex and be substantially dome-shaped as portions of a sphere or an egg. Portions of the articular surface 124 can be configured to at least extend to and/or beyond the normal (undamaged) anatomical shape of the greater tuberosity 26 both superiorly and medially to facilitate articulation by sliding with respect to the undersurface 46 of the acromion 40. For example, with the implant 120 positioned relative to the proximal humerus 22, portions of the articular surface 124 preferably can be between approximately 0-5 mm up to 6 mm and even 7 mm, higher in a superior direction than the maximum normal (undamaged) anatomical height and bony outline of the greater tuberosity 26, and approximately 2-5 up to 6 mm and even 7 mm mm higher in a superior direction than the maximum normal (undamaged) anatomical height and bony outline of the humeral head 24.

Figure 13:
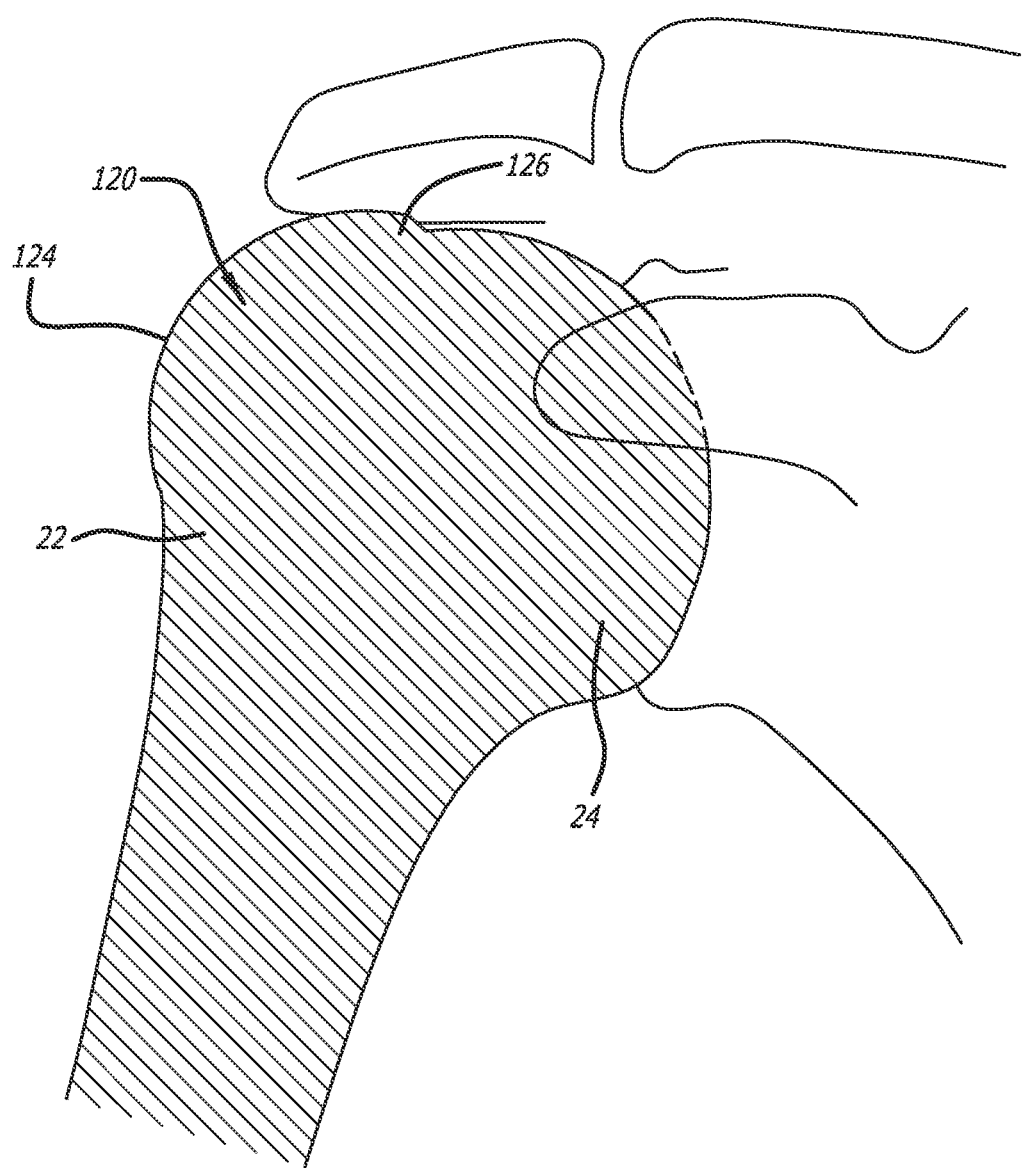
FIG. 13 is a front illustrative view similar to FIG. 11 depicting the second embodiment of the proximal-humerus surface-reconfiguration device and proximal humerus together in cross-section.

The use of the implant 120 serves in reshaping the proximal humerus 22 into the shape depicted in FIG. 13. The protrusion formed by the articular surface 124 serves in moving the proximal humerus 22 inferiorly to facilitate centralization of the humeral head 24 in the shoulder joint 20 through a useful range/arc of shoulder elevation. As such, the use of the implant 120 serves to counter the tendency of superior subluxation in a shoulder joint 20 with a chronic, massive rotator cuff tear.

The implant 120, as depicted in FIGS. 11-13, includes a medial leading edge portion 126 that is blunted and serves to transition the articular surface 124 from the circle 92 to the circle 90. The medial leading edge portion 126 serves to lessen potential erosion of the upper edge 112 of the glenoid 42 due to contact therewith. The medial leading edge portion 126 can be configured to smoothly blend into the remaining portions of the proximal humerus 22 and/or cartilage of the glenohumeral joint 54 adjacent the medial leading edge portion 126 to further inhibit erosion caused by contact with the upper edge 112 during articulation of the shoulder joint 20.

Figure 14:
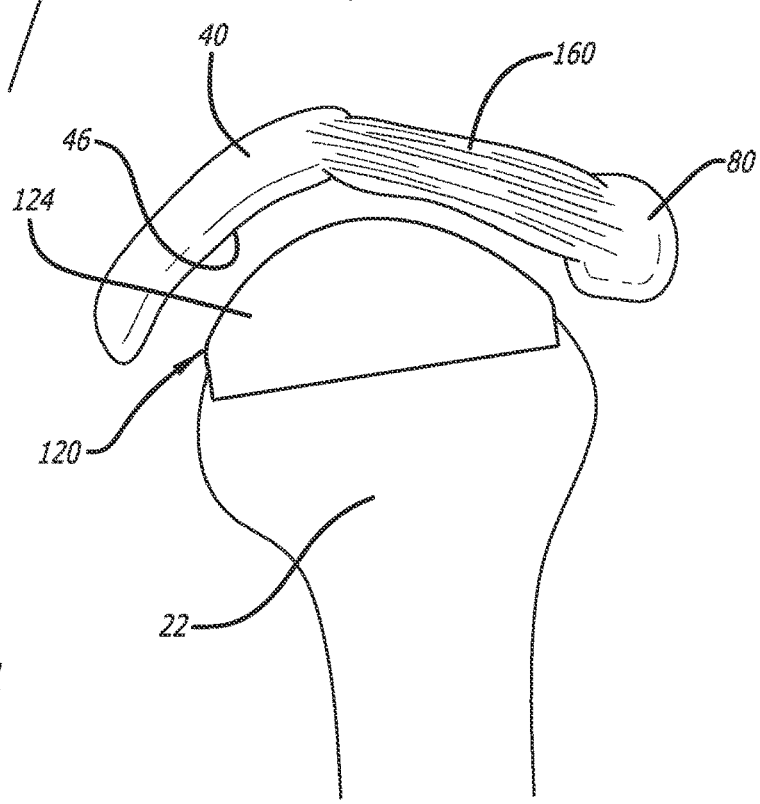
FIG. 14 is a lateral illustrate view depicting the second embodiment of the proximal-humerus surface-reconfiguration device relative to the coracoacromial ligament.

In addition to articulating with respect to the undersurface 46 of the acromion 40, the implant 120 (as well as the below-discussed implant 120' and the implant 130) can also articulate with respect to a coracoacromial ligament 160. As depicted in FIG. 14, the coracoacromial ligament 160 extends between the acromion 40 and a coracoid 80. Furthermore, the articular surfaces 124, 124', and 134, depending on the location of the proximal humerus 22 can also provide smooth gliding contact with the coracoacromial ligament 160.

Figure 15A:
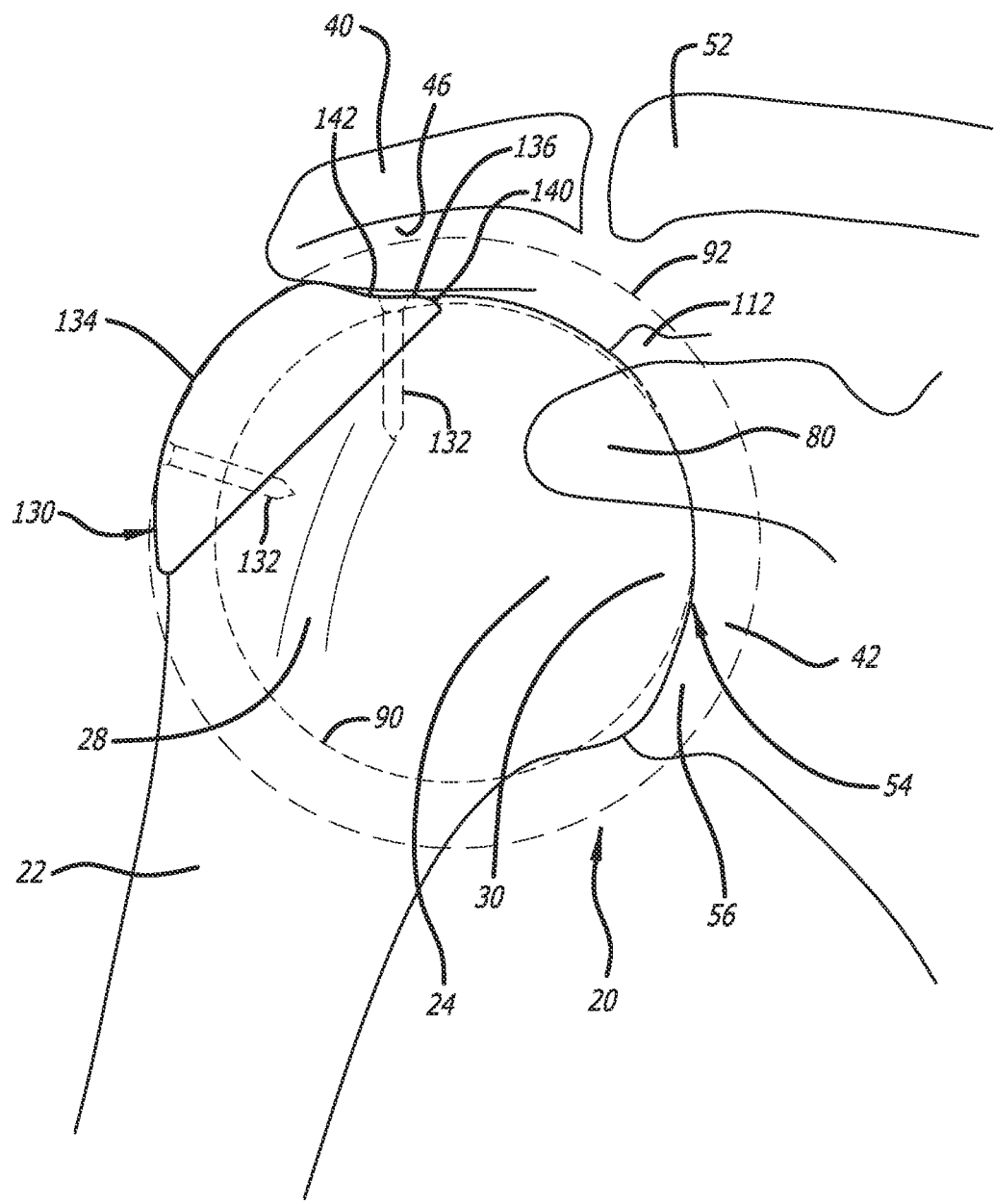
FIG. 15 is a front illustrative view depicting a third embodiment of a proximal-humerus surface-reconfiguration device according to the present disclosure in position relative to a shoulder joint.
Figure 15B:
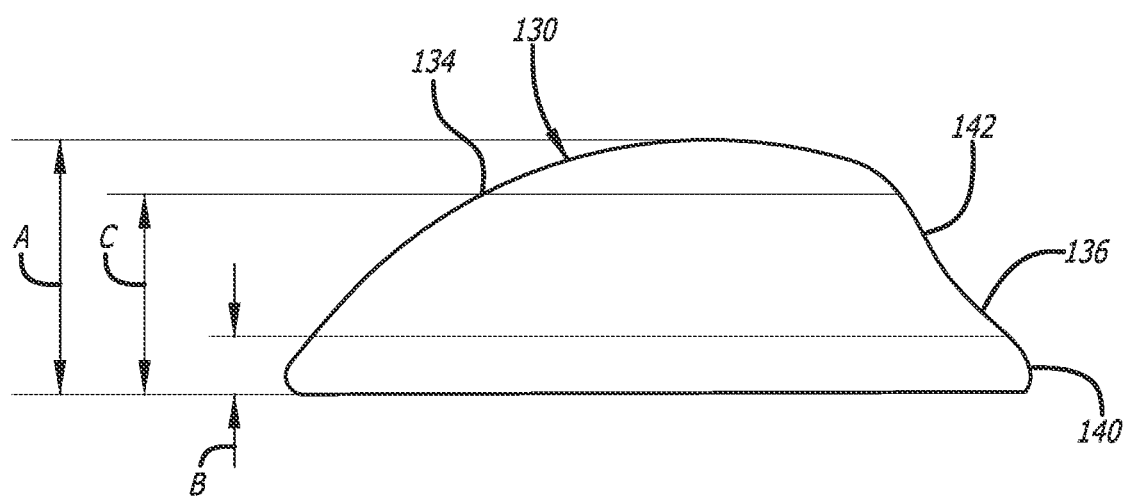

FIG. 15 depicts the third embodiment 130 of the surface-reconfiguration implant. Like the implants 100 and 120, the implant 130 is attached to the proximal humerus 22, overlaps portions of the humeral head 24 and overlaps the greater tuberosity 26, and effectively covers and extends above areas where the portions of the humeral head 24 and the greater tuberosity 26 were or are located. The implant 130 can be partially shaped as a substantially spherical cap. The attachment of the implant 130 to the proximal humerus 22 can be effectuated with fasteners 132 (FIG. 15) such as bone screws.

As depicted in FIG. 15, the implant 130 includes a raised articular surface 134. Like the implants 100 and 120, the articular surface 134 can extend along portions of and within or just slightly out the outermost circle of the circle 92. The articular surface 134 can be at least in part biconvex and be at least in part substantially shaped as portions of a sphere or an egg. Portions of the articular surface 134 can be configured to at least extend to and/or beyond the normal (undamaged) anatomical shape of the greater tuberosity 26 both superiorly and medially to facilitate articulation by sliding with respect to the undersurface 46 of the acromion 40. For example, with the implant 130 positioned relative to the proximal humerus 22, portions of the articular surface 134 preferably can be between approximately 0-5 mm up to 6 mm and even 7 mm higher in a superior direction than the maximum (undamaged) normal anatomical height and bony outline of the greater tuberosity 26, and approximately 0-5 mm up to 6 mm and even 7 mm higher in a superior direction than the maximum normal (undamaged) anatomical height and bony outline of the humeral head 24.

Like that of the articular surface 124, the protrusion formed by the articular surface 134 serves in moving the proximal humerus 22 inferiorly to facilitate centralization of the humeral head 24 in the shoulder joint 20 through a useful range/arc of shoulder elevation. As such, the use of the implant 120 serves to counter the tendency of superior subluxation in a shoulder joint 20 with a chronic, massive rotator cuff tear.

The implant 130 includes a medial leading edge portion 136 that is blunted and indented to further lessen and minimize potential erosion of the upper edge 112 of the glenoid 42 due to contact with the implant 120. The medial leading edge portion 136 is configured to extend around a portion of the perimeter of the implant 130, and is ultimately located at the level of articular cartilage (not shown) between the humeral head 24 and the glenoid 42. The medial leading edge portion 136, as depicted in FIG. 15, includes a nose portion 140 and an indentation 142.

The nose portion 140 can be configured to smoothly blend into the remaining portions of the proximal humerus 22 and/or cartilage of the glenohumeral joint 54 adjacent the medial leading edge portion 126, and the upper edge 112 can slide over the nose portion 140 and into the indentation 142 to further inhibit erosion caused by contact with the upper edge 112. As such, the nose portion 140 can initially slide across the upper edge 112 of the glenoid 42 and into the glenohumeral joint 54, and then the upper edge 112 of the glenoid 42 can be received in the indentation 142 during articulation of the shoulder joint 20. As such, the nose portion 140 and the indentation 142 can further inhibit potential erosion of the upper edge 112 of the glenoid 42, and prevent outward displacement of the proximal humerus 22 relative to the glenoid 42, so that the medial leading edge portion 136 avoids conflict with the upper edge 112 of the glenoid 42 during articulation of the shoulder joint 20.

Figure 16:
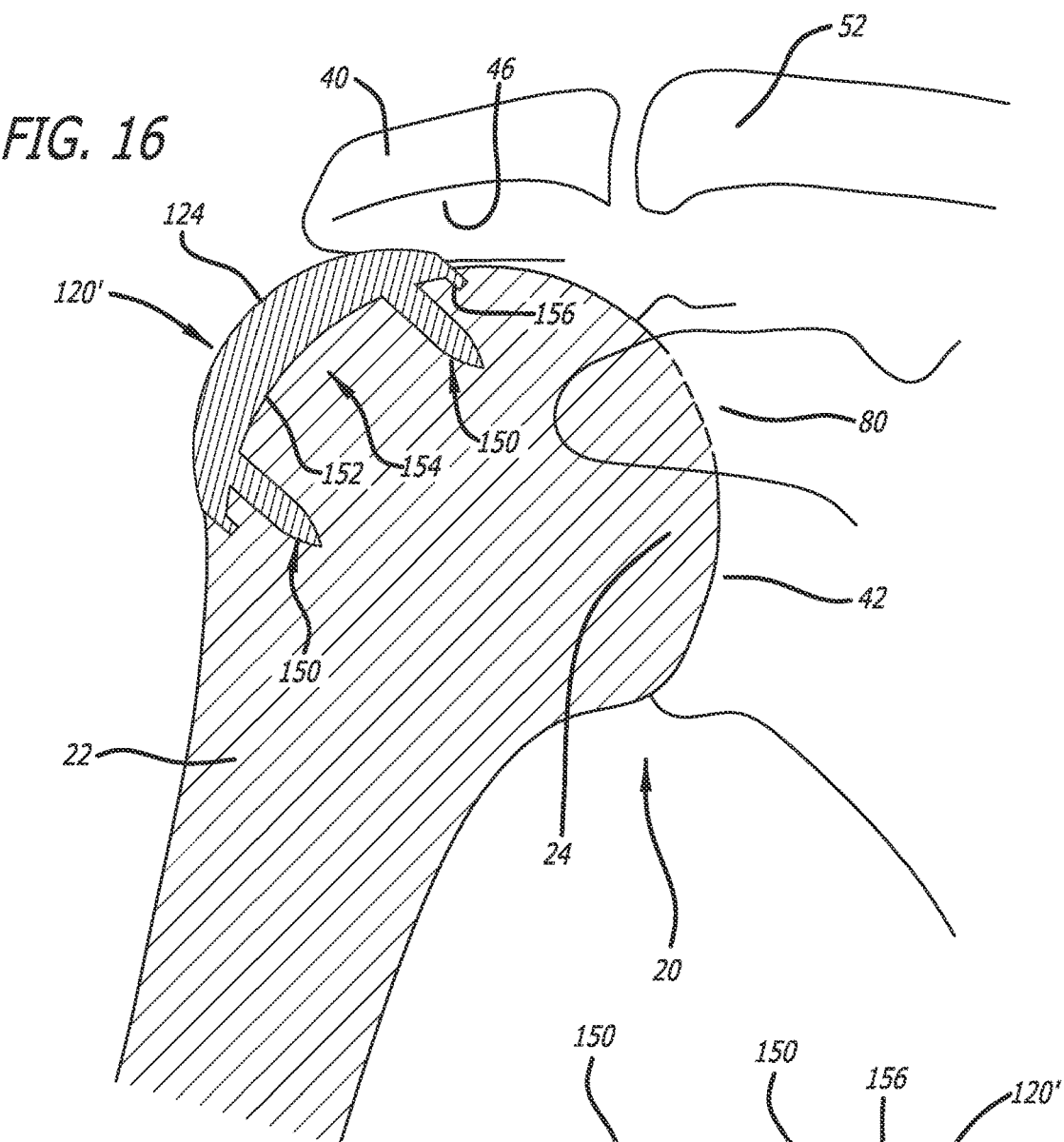
FIG. 16 is a front, partially cross-sectional, illustrative view depicting a modified second embodiment of a proximal-humerus surface-reconfiguration device.
Figure 17:
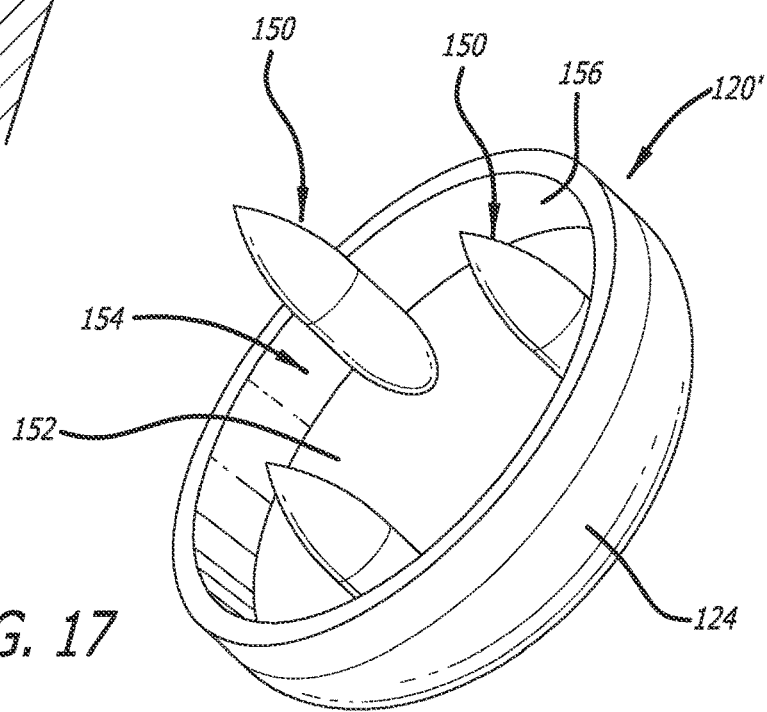
FIG. 17 is a rear, side, perspective view of the modified second embodiment of the proximal-humerus surface-reconfiguration device.

FIGS. 16 and 17 depicted the implant 120', which is a modified embodiment of the implant 120. The implant 120', like the implant 120, includes the articular surface 124. In addition to or in replace of use of the fasteners 122, the implant 120' can include posts or spikes 150 that extend outwardly from an undersurface 152 of the implant 120'. The undersurface 152 can be substantially planar or a substantially concave, and can form a recess 154 with sidewalls 156. As depicted in FIGS. 16 and 17, the undersurface 152 is substantially concave, and the posts or spikes 150 protrude through and out of the recess 154. Each of the implant 120 and the implant 130 can include the posts or spikes 150, the undersurface 152, the recess 154, and the sidewalls 156. When implant 120' is attached to the proximal humerus 22, portions of proximal humerus 22 can be received in the recess 154, and the posts or spikes 150 can be received in apertures or channels (not shown) formed in the proximal humerus 22. Receipt of the posts or spikes 150 in the apertures or channels can create an interference fit between the implant 120' and the proximal humerus 22 to facilitate attachment therebetween.

Each of the implant 120, the implant 120' and the implant 130 include a body portion on which the articular surface 124 and the articular surface 134 are formed. The body portion can be formed as a metallic, bi-convex, spherical, or egg-shaped cap (on which the substantially-spherical articular surfaces 124 and 134 are formed) with a circular or non-circular perimeter, and a substantially planar undersurface or a substantially concave undersurface (FIGS. 15 and 16). When the fasteners 122 and 132 are used, the body portions can each include fastener-receiving apertures for receiving the fasteners 122 and 132 therein. The depths of the fastener-receiving apertures and lengths of the fasteners 122 and 132 can vary depending on the thickness of the body portion. Furthermore, the positions and angles of the fastener-receiving apertures can also vary to provide the fasteners 122 and 132 sufficient purchase in the proximal humerus 22.

If the undersurface of the body portion is substantially planar, portions of the proximal humerus 22 may require removal and contouring to form an attachment surface (not shown) for interfacing with the planar undersurface and attaching the body portion thereto. Furthermore, if the undersurface of the body portion is substantially concave, portions of the proximal humerus 22 may also require removal and contouring to form an attachment surface (not shown) for interfacing with the concave undersurface and attaching the body portion thereto. However, when the undersurface of the body portion is substantially concave, more of the proximal humerus 22 can be left after removal and contouring because portions of the proximal humerus 22 can fit within an interior cavity (not shown) of the body portion formed by the concave undersurface.

Figure 18:
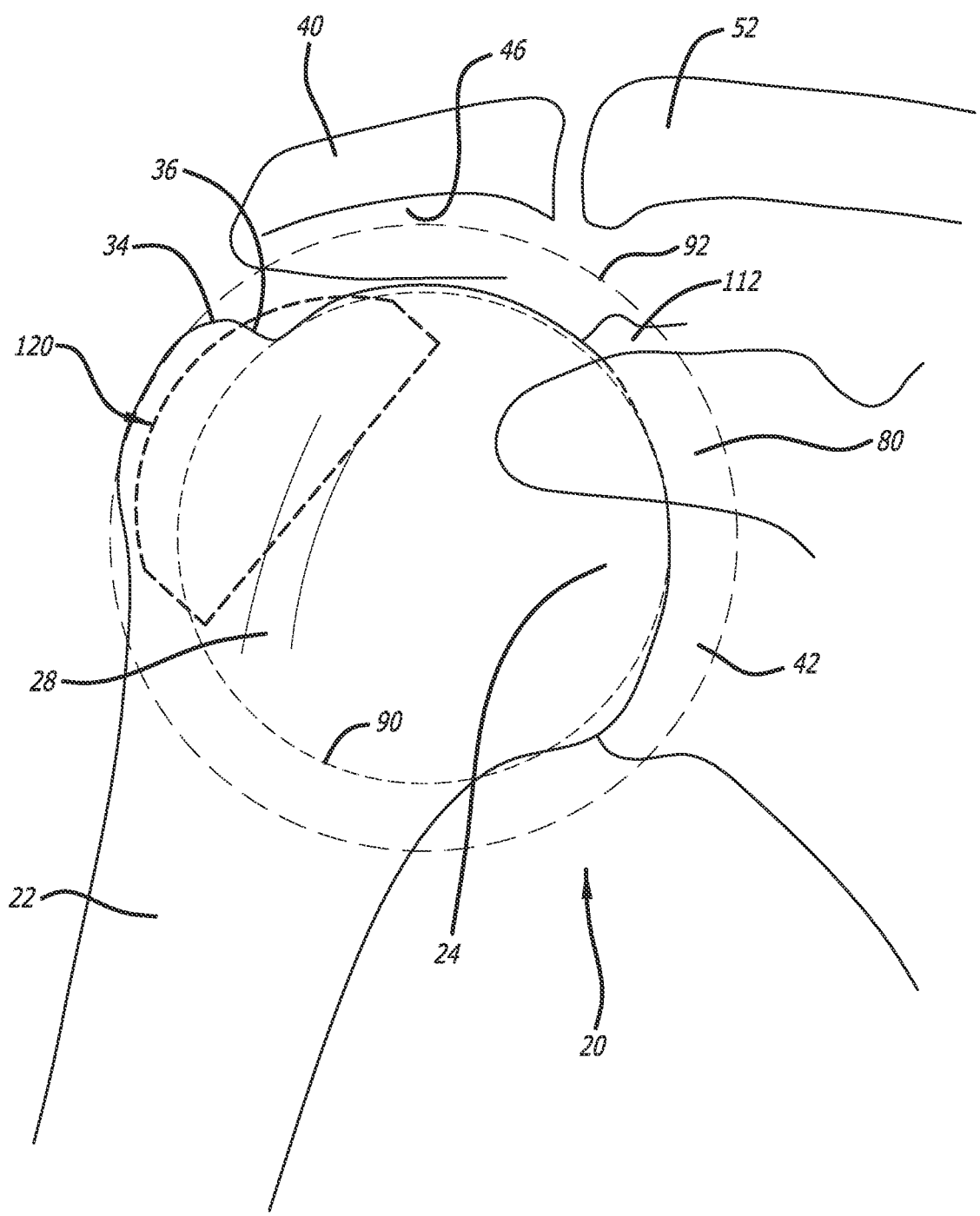
FIG. 18 is a front illustrative view depicting the second embodiment of the proximal-humerus surface-reconfiguration device mispositioned relative to the proximal humerus.

When the implant 100, the implant 120, the implant 120', and the implant 130 are implanted, each of the articular surface 104, the articular surface 124, and the articular surface 134, create a prominence on the proximal humerus 22 that serves to force the proximal humerus 22 downwards relative to the acromion 40. However, if the implant 100, the implant 120, the implant 120', and the implant 130 are improperly implanted, the implants may have no or limited effect on restoring stability to the shoulder joint 20. For example, as depicted in FIG. 18, the implant 120 has been improperly implanted with the implant 120 being located below areas where the portions of the humeral head 24 and the greater tuberosity 26 were or are located. The improperly implanted implant 120 of FIG. 18 does not function like a properly implanted implant 120. With proper implantation of the implant 100, the implant 120, the implant 120', and the implant 130, the humeral head 24 is translated inferiorly using the implant 100, the implant 120, the implant 120', and the implant 130. Such inferior translation of the humeral head 24 serves to counter the tendency of superior subluxation in a shoulder joint 20 with a chronic, massive rotator cuff tear. Lowering of the humeral head 24 correspondingly tightens the deltoid muscle and improves the mechanical level of the deltoid in a shoulder with a massive rotator cuff tear.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

I claim:

1. A surface-reconfiguration implant for creating an articular surface facilitating articulation with an acromion and a glenoid during movement of a shoulder joint, the surface-reconfiguration implant comprising:
   a body portion including at least an undersurface and an articular surface, the undersurface of the body portion being configured to interface with portions of a proximal humerus to facilitate attachment of the body portion thereto, portions of the articular surface extending to and/or beyond at least a normal anatomical shape of an upper portion of a humeral head and a greater tuberosity both superiorly and medially when the body portion is attached to the proximal humerus, the articular surface including a first portion being substantially shaped as portions of one of a sphere and an egg, and a second portion having a medial leading edge portion with a nose portion and an indentation provided adjacent the nose portion, the nose portion being positioned farther medially than the indentation and a perpendicular distance from the undersurface of the body portion to a peak of the nose portion is less than a perpendicular distance from the undersurface of the body portion to a minimum of the indentation, portions of the nose portion being configured to blend into portions of the proximal humerus;
   wherein, when attached to the proximal humerus, the articular surface contacts an undersurface of the acromion, and correspondingly provides inferior translation of the proximal humerus in the shoulder joint.

2. The surface-reconfiguration implant of claim 1, wherein, when attached to the proximal humerus, the nose portion is slidable over an upper edge of the glenoid, and the upper edge of the glenoid is receivable in the indentation during articulation of the shoulder joint.

3. The surface-reconfiguration implant of claim 2, wherein receipt of the upper edge of the glenoid in the indentation serves in preventing outward displacement of the proximal humerus relative to the glenoid.

4. The surface-reconfiguration implant of claim 1, wherein the undersurface of the body portion is one of planar and concave, and the undersurface of the body portion is configured to interface with the proximal humerus after portions thereof have been removed.

5. The surface-reconfiguration implant of claim 1, wherein, from an anterior direction, a portion of a first circle is capable of following an outline of the humeral head of the proximal humerus, and a second circle is capable of being centered on a center of the first circle and has a radius extending to or just beyond the greater tuberosity, the articular surface being configured to extend along portions of and within the second circle.

6. A surface-reconfiguration implant for creating an articular surface facilitating articulation with an acromion and a glenoid during movement of a shoulder joint, the surface-reconfiguration implant comprising:
   a body portion including at least an undersurface and an articular surface, the body portion being configured for attachment to portions of a proximal humerus to extend to and/or beyond a normal anatomical shape of an upper portion of a humeral head and a greater tuberosity both superiorly and medially when the body portion is attached to the proximal humerus, the articular surface including a first portion being substantially dome-shaped, and a second portion having a medial leading edge portion with a nose portion and an indentation provided adjacent the nose portion, the nose portion being positioned farther medially than the indentation, and a perpendicular distance from the undersurface of the body portion to a peak of the nose portion is less than a perpendicular distance from the undersurface of the body portion to a minimum of the indentation, portions of the nose portion being configured to blend into portions of the proximal humerus;
   wherein, when attached to the proximal humerus, the articular surface contacts an undersurface of the acromion, and correspondingly provides inferior translation of the proximal humerus in the shoulder joint.

7. The surface-reconfiguration implant of claim 6, wherein, when attached to the proximal humerus, the nose portion is slidable over an upper edge of the glenoid, and the upper edge of the glenoid is receivable in the indentation during articulation of the shoulder joint.

8. The surface-reconfiguration implant of claim 7, wherein receipt of the upper edge of the glenoid in the indentation serves in preventing outward displacement of the proximal humerus relative to the glenoid.

9. The surface-reconfiguration implant of claim 6, wherein the undersurface of the body portion is one of planar and concave, the undersurface of the body portion being configured to interface with the proximal humerus after portions thereof have been removed.

10. The surface-reconfiguration implant of claim 6, wherein, from an anterior direction, a portion of a first circle is capable of following an outline of the humeral head of the proximal humerus, and a second circle is capable of being centered on a center of the first circle and has a radius extending to or just beyond the greater tuberosity, the articular surface being configured to extend along portions of and within the second circle.

11. A surface-reconfiguration implant for creating an articular surface facilitating articulation with an acromion and a glenoid during movement of a shoulder joint, the surface-reconfiguration implant comprising:
a body portion including at least an undersurface and an articular surface, the undersurface of the body portion being configured to interface with portions of a proximal humerus to facilitate attachment of the body portion thereto, portions of the articular surface extending to and/or beyond at least a normal anatomical shape of an upper portion of a humeral head and a greater tuberosity both superiorly and medially when the body portion is attached to the proximal humerus, the articular surface being at least in part bi-convex including a first convex portion, a second convex portion, and an indentation positioned between the first convex portion and the second convex portion, the second convex portion forming a nose portion being configured to blend into portions of the proximal humerus, the nose portion being positioned farther medially than the first convex portion and the indentation, and a perpendicular distance from the undersurface of the body portion to a peak of the nose portion is less than a perpendicular distance from the undersurface of the body portion to a minimum of the indentation;
wherein, when attached to the proximal humerus, the articular surface contacts an undersurface of the acromion, and correspondingly provides inferior translation of the proximal humerus in the shoulder joint.

12. The surface-reconfiguration implant of claim 11, wherein, when attached to the proximal humerus, the nose portion is slidable over an upper edge of the glenoid, and the upper edge of the glenoid is receivable in the indentation during articulation of the shoulder joint.

13. The surface-reconfiguration implant of claim 12, wherein receipt of the upper edge of the glenoid in the indentation serves in preventing outward displacement of the proximal humerus relative to the glenoid.

14. The surface-reconfiguration implant of claim 11, wherein the undersurface of the body portion is one of planar and concave, and the undersurface of the body portion is configured to interface with the proximal humerus after portions thereof have been removed.

15. The surface-reconfiguration implant of claim 11, wherein, from an anterior direction, a portion of a first circle follows an outline of the humeral head of the proximal humerus, and a second circle centered on a center of the first circle has a radius extending to or just beyond the greater tuberosity, the articular surface being configured to extend along portions of and within the second circle.

* * * * *